United States Patent [19]

Figler et al.

[11] Patent Number: 4,469,480

[45] Date of Patent: Sep. 4, 1984

[54] INTERMITTENT DROP DETECTING METHOD AND APPARATUS

[75] Inventors: Alan A. Figler, Algonquin; Pamela Wilson, Waukegan; Randall A. Zielsdorf, Mundelein, all of Ill.

[73] Assignee: Baxter Travenol Laboratories, Inc., Deerfield, Ill.

[21] Appl. No.: 465,707

[22] Filed: Feb. 11, 1983

[51] Int. Cl.³ ............................................ A61M 5/16
[52] U.S. Cl. .................................. 604/52; 604/65; 604/245; 604/246; 222/14; 222/59; 222/71; 324/71.1; 128/DIG. 13
[58] Field of Search .......................... 604/31, 51–53, 604/65, 67, 50, 245–246, 250, 253; 222/14, 52, 59, 71, 76; 250/222.1, 222.2; 368/107; 324/71.1, 71.4; 371/28; 128/DIG. 13

[56] References Cited

U.S. PATENT DOCUMENTS

| | | | |
|---|---|---|---|
| 3,655,095 | 4/1972 | Kienitz | 222/59 |
| 3,736,930 | 6/1973 | Georgi | 128/DIG. 13 |
| 3,800,794 | 4/1974 | Georgi | 604/52 |
| 4,037,598 | 7/1977 | Georgi | 604/253 |
| 4,038,982 | 8/1977 | Burke et al. | 604/253 |
| 4,181,130 | 1/1980 | Bailey | 604/65 |
| 4,261,388 | 4/1981 | Shelton | 604/253 |
| 4,383,252 | 5/1983 | Purcell et al. | 604/31 |
| 4,397,642 | 8/1983 | Lamadrid | 604/245 |
| 4,412,175 | 10/1983 | Maynarez | 324/71.1 |

FOREIGN PATENT DOCUMENTS 1253817 11/1971 United Kingdom .

Primary Examiner—C. Fred Rosenbaum
Assistant Examiner—Michelle N. Lester
Attorney, Agent, or Firm—Paul C. Flattery; Robert A. Benziger; John T. Winburn

[57] ABSTRACT

The present invention provides an accurate method and apparatus for monitoring the drop flow rate from a fluid source. The method and apparatus allows for an intermittent drop flow rate by accumulating a weighted drop period rate error factor which is adjusted for each drop period detected.

A drop period window is adjusted by each drop period and is utilized to determine if the current drop period is within the window indicating a normal operation. Drop periods outside the window cause a factor to be added to the accumulated error factor and drop periods within the window cause a factor to be subtracted from the accumulated error factor. This allows good periods to offset bad periods, so that minor fluctuations in the drop periods during normal operation can be ignored.

12 Claims, 4 Drawing Figures

INTERMITTENT DROP DETECTING METHOD AND APPARATUS

BACKGROUND OF THE INVENTION

The present invention pertains to an improved fluid drop detection method and apparatus. More particularly, the present invention is directed to a method and apparatus for detecting drops over a period of time and comparing the current drop time period to limits defined by previous drops.

The invention is contemplated specifically for use in the administration of parenteral solutions to patients in hospitals and the like, but it also can be utilized for detecting and controlling drop flow of any liquid in precise quantities over a desired period of time into chemical or biological reactors, industrial processes, and the like.

While the administration of parenteral solutions is a common practice in hospitals, and great quantities of equipment of many different types are sold for the purpose of providing such administration, in many instances the medical situation calls for the administration of precisely controlled amounts of medication on a continuous drip basis over a period which may last several days or weeks. Cancer chemotherapy agents, for example, may be administered in this manner.

For these agents, and for many other medications, they must, of course be administered to the patient in sufficient quantities to be effective, and often a uniform, continuous low volume dose is required. At the same time, an accidental increase in the flow rate can be life threatening in the case of some medications, and thus totally must be avoided.

The drop flow from conventional, gravity-operated parenteral solution equipment is subject to a wide range of variable situations, such as fluid viscosities, tubing properties and resonant phenomenon. These and other effects can cause intermittent drop flow.

In the prior art, numerous patents exist which suggest various systems for controlling the flow of parenteral solution through a large assortment of electronic devices which purportedly provide improved flow accuracy. As a typical example of such prior art, drops of the solution are formed and fall through a conventional drip chamber in an administration set and are detected as they fall by a drop detector which can operate on photometric principles, by sensing variations in capacitance, or the like. A flow control clamp valve or other occlusion device is provided in the flow conduit and is controlled by a feedback mechanism, typically electronic, for sensing the drop rate in the drip chamber and appropriately controlling the valve so that the drop rate is kept within desired parameters.

In the prior art, a pump often is used to propel the solution through the set. This carries its own hierarchy of risks, and requires the presence of safety systems to prevent the pumping of air into the patient in the event that the source of parenteral solution runs dry. Such safety systems are, of course, subject to breakdown and failure, and the consequences of that also potentially are fatal.

It therefore is preferable, for safety and simplicity, to utilize a gravity operated system which precisely measures amounts of parenteral solution to a patient. One such system is disclosed and claimed in co-pending U.S. Application Ser. No. 336,154, filed Jan. 6, 1982, in the name of Rene Lamadrid for MOTOR DRIVEN OCCLUSION CONTROLLER FOR LIQUID INFUSION AND THE LIKE, which application is assigned to the assignee of the present invention and is incorporated herein by reference.

As disclosed therein, an integral part of the system is a drop detector which detects drops as they pass through a drip chamber. In this system a fixed drop rate is selected and the actual drop rate is compared thereto to provide a control signal to the occlusion controller. The precision of the drop detection is critical in this type of system.

SUMMARY OF THE INVENTION

In accordance with the present invention, a method and apparatus is provided to precisely monitor the drop flow rate from a fluid source. The invention allows for variations in the drop flow rate by accumulating a weighted rate error factor which can be adjusted by each drop period detected.

Preferably each drop period or interval is compared against both a slow rate limit and a fast rate limit. The limits are set proportional to the previous drop period. The accumulated total is compared to an error threshold, which is set to ignore minor fluctuations in a number of consecutive drop periods. The accumulated total also can be averaged over a multiple number of drop periods by adding an error factor for each drop period which is outside of the limit and subtracting an error factor for each drop period which is within the limit.

DETAILED DESCRIPTION

Figure 1:
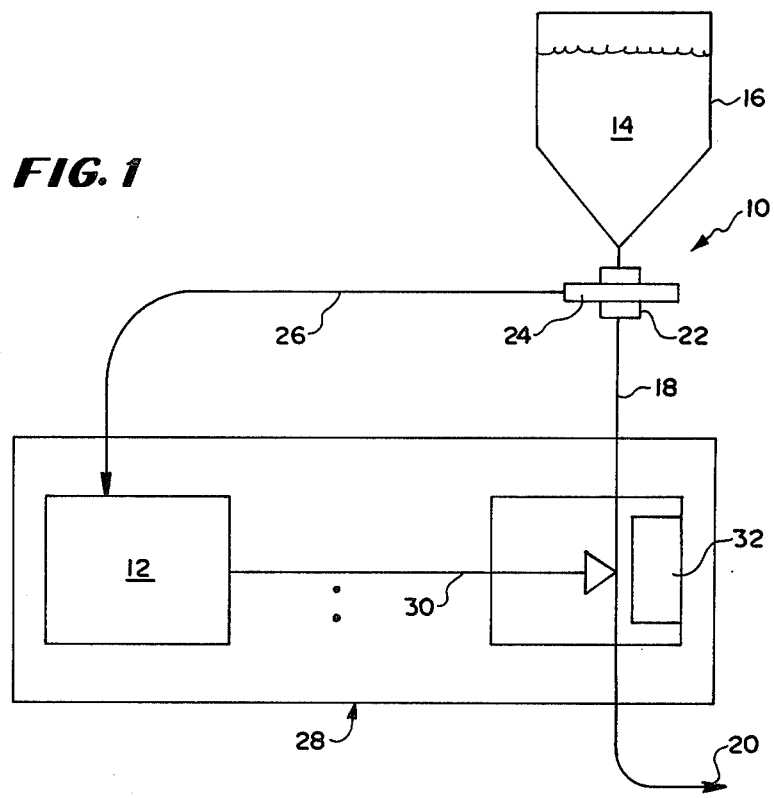
FIG. 1 is a schematic diagram of a drop detection and occlusion system.

Referring to FIG. 1, there is shown diagramatically a drop detecting and occlusion system 10, which can incorporate the present invention of a drop period or interval detecting system 12. A fluid 14 to be controlled, such as a parenteral solution, is contained in a fluid source or container 16. The fluid source 16 can be part of a conventional parenteral solution set which includes a flexible, collapsible tubing 18 through which the fluid 14 passes to a patient or other communication set as indicated by an arrow 20. The fluid 14 passes through a drip chamber 22 which can be of any conventional design.

A drop detector 24 is provided adjacent the drip chamber 22 which detects drops of the fluid 14 as they pass through the chamber. The drop detector 24 can be of any conventional design and preferably is an optical type of detector, such as that described in the above-referenced application. Other types of detectors can be utilized such as those which utilize electrical capacitance principles.

When a fluid drop is detected by the detector 24, an electrical signal is coupled over a line 26 to the period detector 12. The period detector 12 can include, be coupled to, or be a portion of an occlusion mechanism 28. The details of one such occlusion mechanism are fully disclosed in the above-referenced application.

In operation, the occlusion mechanism 28 includes a piston or clamp member 30, diagramatically illustrated. In accordance with the flow rate sensed by the drip detector 24, the clamp member 30 is positioned to clamp the tubing 18 against a stop plate 32. The clamping force applied to the tubing 18 is increased when the flow is too rapid and decreased when the flow is too slow. In emergencies or malfunctions, the clamping force preferably is such as to automatically terminate fluid flow.

Figure 2:
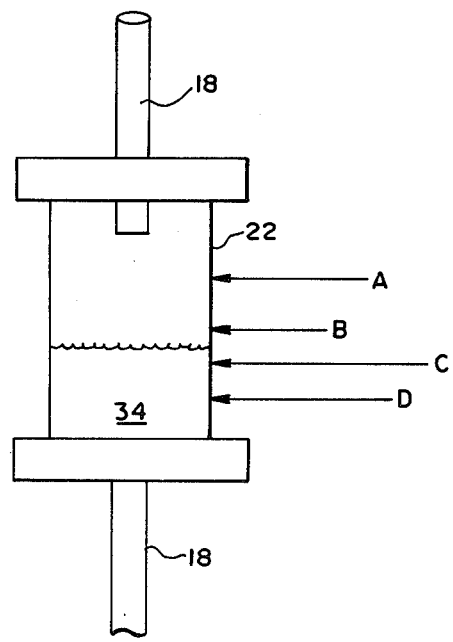
FIG. 2 is a schematic diagram of a drip chamber illustrating possible drop detector locations.

Referring to FIG. 2, the positioning of the light path or detection level of the drop detector 24 is illustrated by the arrows A, B, C and D. In normal operation, the light path or comparable drop detection level is set at level A. At this level, the drops are sensed individually without interference from any of the accumulated fluid 34. However, the outside configuration of the drip chambers can vary significantly and some chambers are tapered. These configurations, misalignment and intermittent conditions all can cause a false drop count and variations in the flow rate.

For example, if the detection level is set inadvertently at level B, then the detector 24 can also pick up splashes to result in a false high count or too rapid a drop interval. The occlusion mechanism 28 will then apply more pressure to the tubing 18 to reduce the fluid flow, because of the false count. If the detection level is positioned at level C right below the surface of the accumulated fluid 34, then the detector 24 can pick up air bubbles and other turbulence and cause the drop flow to be almost or completely cut off. At level C, one of the most dangerous situations also can occur. In some cases, only some of the drops are detected which can cause the occlusion mechanism 28 to open up and an over infusion of the patient can occur. The system and method of the invention prevent this from occurring, while ignoring occasional false or spurious drop detection signals. If positioned at level D, the system will time out after a predetermined no count period, since essentially no drops will be detected.

Figure 3:
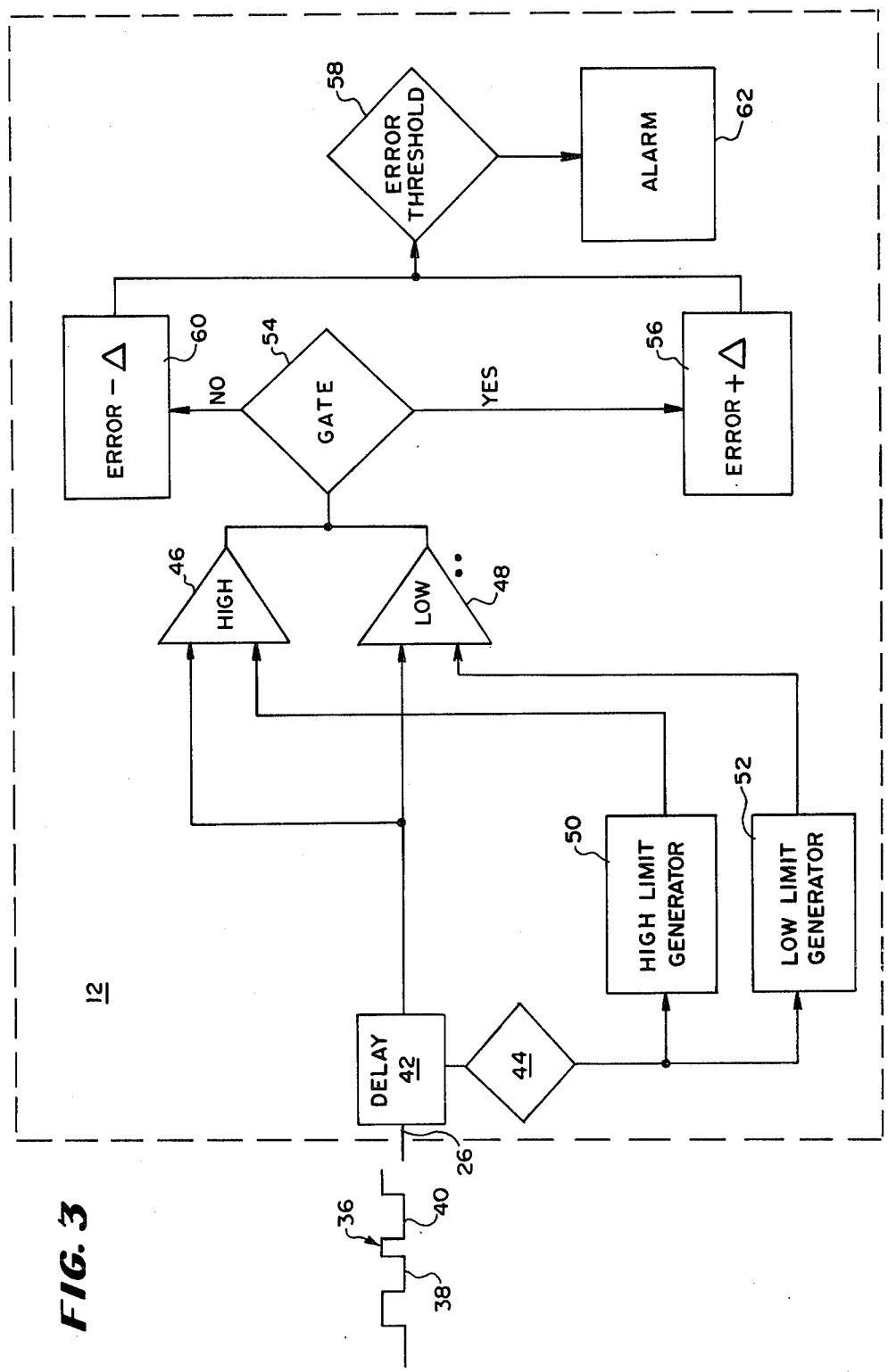
FIG. 3 is a block diagram of a drop detecting apparatus of the present invention.

Referring to FIG. 3, the drop period detector 12 is best illustrated. A pulse string 36 of drop detection signals is coupled to the detector 12 over the line 26. The signal string 36 includes a current drop period signal 38 and a previous drop period signal 40. The signal string 36 preferably is coupled to a delay timer 42.

The delay timer 42 is utilized as a grace period to ignore the start-up or initial drop rate while the drop rate stabilizes. The grace period can also be utilized by the operator when the flow rate is adjusted during operation. Once the delay timer grace period times out, then each current period is compared against limits which are related to the previous time period.

Utilizing, for convenience, the current period 38 and the previous period 40, the current period 38 is coupled through the delay 42 to a one period time delay 44 which has an output of the previous period 40. The current period 38 is also coupled to a limit comparing circuit, which preferably includes a high or slow drop limit comparator 46 and a low or fast drop limit comparator 48. The current period 38 is coupled to a first input of each comparator 46 and 48.

The output of the period delay 44 is coupled to both a high or slow limit setting generator 50 and a low or fast limit setting generator 52. The slow limit generator 50 multiplies a selected factor, preferably greater than unity, against the previous period 40 and adds a second selected factor to adjust the slow window limit of the comparator 46. The fast limit generator 52 multiplies a selected factor, preferably less than unity, against the previous period 40 and substracts another selected factor to adjust the fast window limit of the comparator 48. Thus, the current drop period 38 is compared to a window set by the generators 50 and 52, which is adjusted by the previous period 40.

If the current period 38 is too slow or long and hence falls outside the high limit of the comparator 46 or it is too fast or short and hence falls outside the low limit of the comparator 48, an error signal is sent by a gate 54 to a bad drop period error accumulator 56. The accumulator 56 adds a selected factor to the total accumulated error factor which is then coupled to and compared with a predetermined threshold limit in a threshold error comparator 58.

If the current period 38 is not too slow or long and hence falls within the high limit of the comparator 46 and it is not too fast or short and hence falls within the low limit of the comparator 48, a good drop signal is sent by the gate to an accumulator 60. The accumulator 60 subtracts a selected factor from the total accumulated error factor which can then be coupled to the threshold error comparator 58 or which can just be utilized to decrease the accumulated error factor. The accumulated error factor preferably is reset in the other accumulator 56 or 60 after each pulse to keep the error factor the same in each accumulator.

If the accumulated error factor is greater than the threshold limit, a signal can be coupled to an alarm 62. The alarm 62 can be audio, visual or both and can also cause the shut down of the fluid flow, if desired.

With this operation, a window and correction factor can be selected such that transient bad pulses are cancelled out by good pulses. For example, in a typical IV operation, the drop rate can be 20 drops per minute and the correction factor can be set so that a predetermined number of drops in a row have to be bad before an alarm. For example, with 20 drops per minute, the detector 12 can be set to alarm after four consecutive bad drops or four out of six, etc. This allows the inevitable transient bad drops, such as caused by hitting the fluid container 16, etc., to be ignored by the system.

Figure 4:
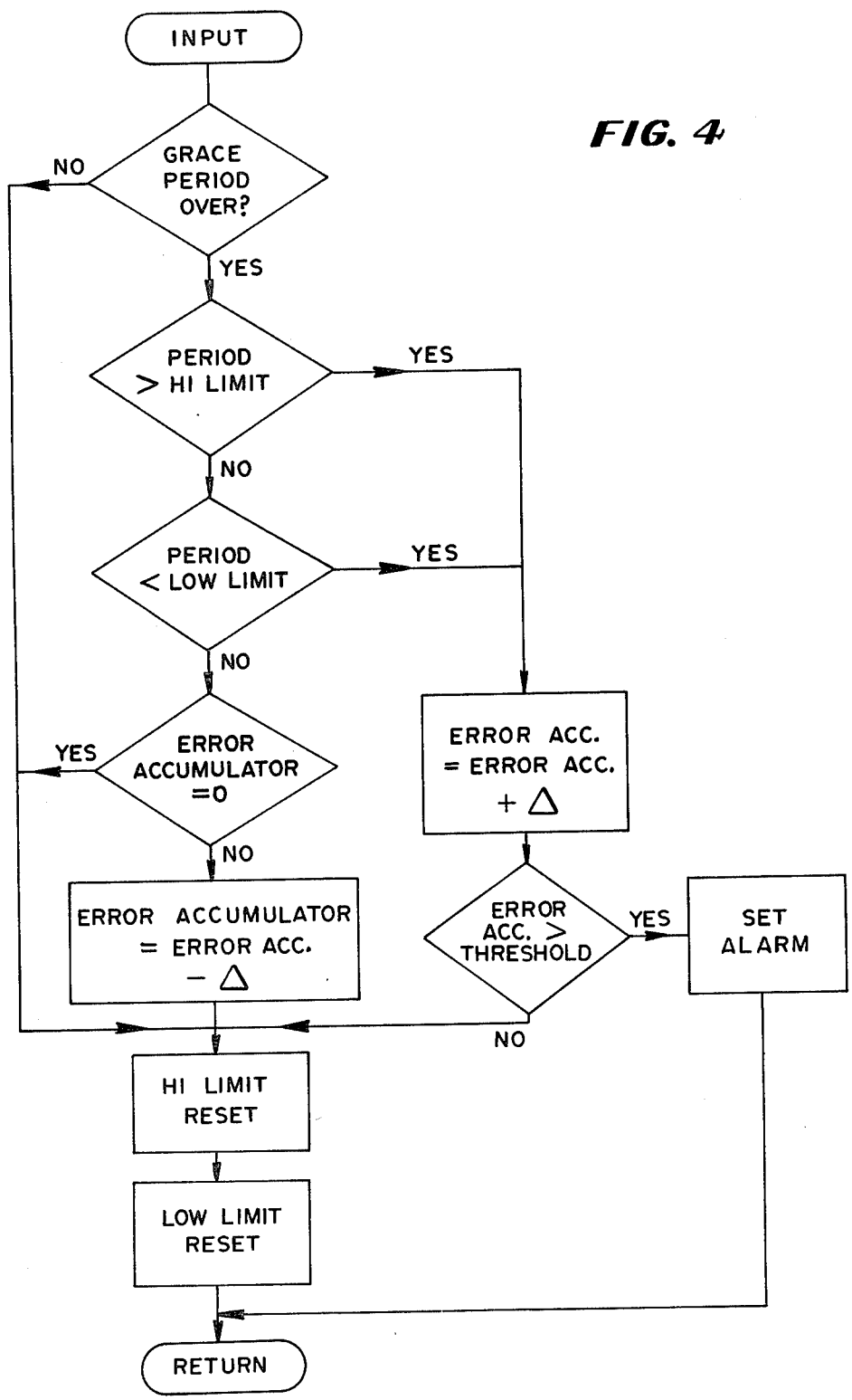
FIG. 4 is a flow chart configured in accordance with the present invention.

Referring now to FIG. 4, there is illustrated a flow diagram of the preferred method of the invention. The drop period is ignored if the grace period is not yet over. If the grace period is over, the drop period is first compared to the high or slow limit. If the period is outside the limit the error accumulator adds an error factor to the accumulated error and then compares the total accumulated error factor to the alarm threshold. If the accumulated error factor is greater than the threshold limit, then an alarm is set. If the accumulated error factor is less than the alarm threshold, then the current period is utilized to reset the window as described below.

If the period is less than the high or slow limit, the period is then compared to the low or fast limit. If it is outside the fast limit, the error accumulator is acted on as with the slow limit described above. If the period is not outside the fast limit, the accumulated error is checked to see if it is zero. If it is zero, the period is utilized to reset the limits, but does not change the accumulated error since it preferably is never allowed to go below zero. This allows the system 12 to react quickly to bad drop periods, no matter how long the system has been in operation without bad drop periods.

If, however, the accumulated error factor is not zero, then a factor is subtracted from the accumulated error factor, which allows good periods to cancel out bad periods. The good period is then utilized to reset the window limits. The window limits preferably are reset for each drop period by multiplying the period by a factor greater than unity and adding an adjustment factor to the product for the high limit. The low limit is reset by multiplying the period by a factor less than unity and subtracting an adjustment factor from the product. This completes the cycle, which is adjusted for each drop period.

Modifications and variations of the present invention are possible in light of the above teachings. Depending upon the type of drop flow operation, only one limit (low or high) need be utilized. Further, the factors and drop periods can be selected as desired. Also, the order of limit comparison is of course selected as desired. It is therefore to be understood that within the scope of the appended claims the invention may be practiced, otherwise than as specifically described.

What is claimed and desired to be secured by Letters Patent of the United States is:

1. A method of monitoring drop flow rate from a fluid source, comprising:
   detecting the time period between drops of fluid;
   comparing a current time period with at least one limit defined by a previous time period;
   adding an error factor to an accumulated error total if said current time period is not within said limit;
   comparing said accumulated error total to a predetermined accumulated error threshold limit; and
   setting an alarm if said accumulated error total is greater than said predetermined threshold limit.

2. The method as defined in claim 1 further including:
   comparing said current time period with a slow flow limit and a fast flow limit, each limit being defined by a previous time period; and
   adding an error factor to the accumulated error total if said current time period is greater than said fast flow limit or less than said slow flow limit.

3. The method as defined in claim 2 including:
   setting said slow flow limit by adjusting the limit by a first factor proportional to the time period previous to said current time period and setting said high flow limit by adjusting the limit by a second factor proportional to said previous time period.

4. The method as defined in claim 2 further including:
   subtracting an error factor from the accumulated error total if said current time period is less than said fast flow limit and greater than said slow flow limit.

5. The method as defined in claim 4 including:
   determining if the accumulated error total is greater than zero, and subtracting the error factor only if the error total is greater than zero.

6. The method as defined in claim 1 including:
   determining if a grace time period has elapsed, and comparing the current time period with the limit only if the grace time period has elapsed.

7. An apparatus for monitoring drop flow rate from a fluid source, comprising:
   means for detecting the time period between drops of fluid;
   means for comparing a current time period with at least one limit defined by a previous time period;
   means for adding an error factor to an accumulated error total if said current time period is not within said limit;
   means for comparing said accumulated error total to a predetermined accumulated error threshold limit; and
   means for setting an alarm if said accumulated error total is greater than said predetermined threshold limit.

8. The apparatus as defined in claim 7 further including:
   means for comparing said current time period with a slow flow limit and a fast flow limit, each limit being defined by a previous time period; and
   means for adding an error factor to the accumulated error total if said current time period is greater than said fast flow limit or less than said slow flow limit.

9. The apparatus as defined in claim 8 including:
   means for setting said slow flow limit by adjusting the limit by a first factor proportional to the time period previous to said current time period; and,
   means for setting said high flow limit by adjusting the limit by a second factor proportional to said previous time period.

10. The apparatus as defined in claim 8 further including:
    means for subtracting an error factor from the accumulated error total if said current time period is less than said fast flow limit and greater than said slow flow limit.

11. The apparatus as defined in claim 10 including:
    means for determining if said accumulated error total is greater than zero, said error subtracting means subtracting the error factor only if the error total is greater than zero.

12. The apparatus as defined in claim 7 including:
    means for determining if a grace time period has elapsed, said time comparing means comparing the current time period to the limit only if the grace time period has elapsed.

* * * * *